US012788855B2

(12) United States Patent
Kusters et al.

(10) Patent No.: US 12,788,855 B2
(45) Date of Patent: Nov. 10, 2026

(54) SYSTEMS AND METHODS FOR MONITORING A FLUID PROCEDURE

(71) Applicant: Fenwal, Inc., Lake Zurich, IL (US)

(72) Inventors: Benjamin E Kusters, Pleasant Prairie, WI (US); Kyungyoon Min, Kildeer, IL (US)

(73) Assignee: Fenwal, Inc., Lake Zurich, IL (US)

(*) Notice: Subject to any disclaimer, the term of this patent is extended or adjusted under 35 U.S.C. 154(b) by 884 days.

(21) Appl. No.: 18/125,094

(22) Filed: Mar. 22, 2023

(65) Prior Publication Data

US 2023/0218807 A1 Jul. 13, 2023

Related U.S. Application Data

(63) Continuation of application No. 16/101,185, filed on Aug. 10, 2018, now Pat. No. 11,633,524.

(60) Provisional application No. 62/544,141, filed on Aug. 11, 2017.

(51) Int. Cl.
*A61M 1/16* (2006.01)
*A61M 1/02* (2006.01)
(Continued)

(52) U.S. Cl.
CPC ........ *A61M 1/1603* (2014.02); *A61M 1/0272* (2013.01); *A61M 1/306* (2014.02);
(Continued)

(58) Field of Classification Search
CPC .. A61M 1/1603; A61M 1/0272; A61M 1/306; A61M 1/362227; A61M 1/36224;
(Continued)

(56) References Cited

U.S. PATENT DOCUMENTS 5,868,696 A 2/1999 Giesler et al.
6,582,349 B1 6/2003 Cantu et al.
(Continued)

FOREIGN PATENT DOCUMENTS

WO WO 2014/039086 A1 3/2014

OTHER PUBLICATIONS

Extended European Search Report for Application No. 25159116.0 dated Jul. 4, 2025.

*Primary Examiner* — Jessica Arble
(74) *Attorney, Agent, or Firm* — Cook Alex Ltd.

(57) ABSTRACT

A computer-implemented method comprises providing a fluid circuit comprising fluid pathways configured to mount and associate with a durable processing device comprising a pressure sensor in communication with a controller and a fluid pathway. A container is connected to the pressure sensor and may receive a volume of fluid. A change in pressure values between a first and second time is measured from when the volume of fluid is not in communication with the pressure sensor to when the volume of fluid is in communication with the pressure sensor, the volume of fluid within the container or a presence or absence of a fluid connection to the fluid pathway based on the change in pressure values is determined, and a response action is executed if the volume of fluid within the container is not within an authorized volume range for the time period, or if a fluid connection is unauthorized.

20 Claims, 5 Drawing Sheets

(51) Int. Cl.

| | |
|---|---|
| ***A61M 1/30*** | (2006.01) |
| ***A61M 1/34*** | (2006.01) |
| ***A61M 1/36*** | (2006.01) |
| ***A61M 5/168*** | (2006.01) |

(52) U.S. Cl.
CPC .. *A61M 1/362227* (2022.05); *A61M 1/36224* (2022.05); *A61M 1/362265* (2022.05); *A61M 1/367* (2013.01); *A61M 1/3693* (2013.01); *A61M 1/3696* (2014.02); *A61M 5/16845* (2013.01); *A61M 5/16854* (2013.01); *A61M 1/3403* (2014.02); *A61M 1/362266* (2022.05); *A61M 2205/14* (2013.01); *A61M 2205/15* (2013.01); *A61M 2205/3331* (2013.01); *A61M 2205/3334* (2013.01); *A61M 2205/3393* (2013.01)

(58) Field of Classification Search
CPC ............ A61M 1/362265; A61M 1/367; A61M 1/3693; A61M 1/3696; A61M 5/16845; A61M 5/16854; A61M 1/3404; A61M 1/362266; A61M 2205/14; A61M 2205/15; A61M 2205/3331; A61M 2205/3334; A61M 2204/3393; A61M 1/0281; A61M 1/3643
See application file for complete search history.

(56) References Cited

U.S. PATENT DOCUMENTS

| | | | | |
|---|---|---|---|---|
| 2005/0107923 | A1* | 5/2005 | Vanderveen | G16H 20/17 700/282 |
| 2005/0145010 | A1 | 7/2005 | Vanderveen et al. | |
| 2006/0178611 | A9* | 8/2006 | Westberg | A61M 1/36222 604/6.03 |
| 2006/0270971 | A1* | 11/2006 | Gelfand | A61M 5/1723 604/151 |
| 2017/0326282 | A1 | 11/2017 | Wilt et al. | |
| 2018/0147346 | A1 | 5/2018 | Grosse-Wentrup et al. | |
| 2020/0215249 | A1* | 7/2020 | Griessmann | A61M 1/14 |

* cited by examiner

SYSTEMS AND METHODS FOR MONITORING A FLUID PROCEDURE

CROSS-REFERENCE TO RELATED APPLICATIONS

This application is a continuation of U.S. patent application Ser. No. 16/101,185, filed Aug. 10, 2018, which claims the benefit of U.S. Provisional Patent App. No. 62/544,141, filed Aug. 11, 2017, each of which is expressly incorporated herein by reference in its entirety.

The present disclosure relates generally to monitoring fluid flow through a fluid circuit and, in particular to systems and methods for monitoring and controlling fluid flow through a medical fluid circuit using hydrostatic pressure.

BACKGROUND

A variety of available blood processing systems allows for the collection and processing of particular blood components, rather than whole blood, from donors or patients. In the case of a blood donor, whole blood is drawn from the donor, a desired blood constituent isolated and collected, and the remaining blood components returned to the donor. By removing only particular constituents rather than whole blood, it takes the donor's body a shorter time period to recover to normal blood levels, thereby increasing the frequency with which the donor may donate blood. It is beneficial to increase in this manner the overall supply of blood constituents made available for health care, such as red blood cells (RBCs), leukocytes, plasma, and/or platelets, etc.

The separation phase of blood components from whole blood may be achieved through a spinning membrane or centrifugation, in which whole blood is passed through a centrifuge or membrane after it is withdrawn from the patient. To avoid contamination and possible infection of the patient, the blood is preferably contained within a sealed, sterile fluid flow system during the entire separation process. Typical blood processing systems thus may include a permanent, reusable hardware assembly containing the hardware (drive system, pumps, valve actuators, programmable controller, and the like) that pumps the blood, and a disposable, sealed and sterile fluid circuit that is mounted in cooperation on the hardware. In the case of separation via centrifugation, the hardware assembly includes a centrifuge that may engage and spin a separation chamber of the disposable fluid circuit during a blood separation step. The blood, however, may make actual contact only with the fluid circuit, which assembly may be used only once and then discarded. In the case of separation via a spinning membrane, a disposable single-use spinning membrane may be used in cooperation with the hardware assembly and disposable fluid circuit.

In the case of separation via centrifugation, as the whole blood is spun by the centrifuge, the heavier (greater specific gravity) components, such as red blood cells, move radially outwardly away from the center of rotation toward the outer or "high-G" wall of the separation chamber of the fluid circuit. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber of the fluid circuit.

In the case of separation via a spinning membrane, whole blood may be spun within a disposable spinning membrane, rather than within a separation chamber of a fluid circuit. Larger molecules, such as red blood cells, may be retained within one side of the membrane, while the smaller molecules, such as plasma, may escape through the pores of the membrane to the other side of the membrane. Various ones of these components can be selectively removed from the whole blood by forming appropriately located outlet ports in the housing of the membrane column. Various types of columns with different pore sizes may be used, depending on the components to be separated.

It is common for two or more medical solution containers to be used simultaneously during blood processing procedures. For example, various combinations of saline solution bags, anti-coagulant bags, RBC additive solution bags, platelet additive solution bags, and/or a variety of replacement fluids, such as albumin, RBCs, plasma, etc. may be used in a blood processing procedure. Although these solutions have very different functions and properties, the containers in which they are held may be similar in appearance, and it may often be up to a human operator to make sure that a solution container is connected to the correct fluid pathway.

SUMMARY

According to an exemplary embodiment, the present disclosure is directed to a fluid processing system for monitoring fluid flow in a medical fluid procedure. A fluid circuit comprises a plurality of fluid pathways configured to mount and associate with a durable processing device controlled by a programmable controller. The durable processing device comprises a pressure sensor in communication with the programmable controller and a fluid pathway. A container part of the fluid circuit is configured for fluid communication with the pressure sensor and configured to receive a volume of fluid. The controller is configured to initiate a phase of the medical fluid procedure associated by the controller with a plurality of ranges of pressure values authorized at specific times for the pressure sensor, receive a first pressure value from the pressure sensor measured at a first time during the phase when the volume of fluid is not in fluid communication with the pressure sensor, receive a second pressure value from the pressure sensor measured at a second time during the phase when the volume of fluid is in fluid communication with the pressure sensor, compare a difference between the second pressure value and the first pressure value to an authorized range of pressure values, and execute a response action if the difference is not within the authorized range of pressure values.

According to an exemplary embodiment, the present disclosure is directed to a computer-implemented method for operating and monitoring a medical device and its disposable component used in a fluid procedure. The method comprises providing a fluid circuit comprising a plurality of fluid pathways configured to mount and associate with a durable processing device controlled by a programmable controller. The durable processing device comprises a pressure sensor in communication with the programmable controller and a fluid pathway. A container part of the fluid circuit is configured for fluid communication with the pressure sensor and configured to receive a volume of fluid. The method also comprises measuring a change in pressure values between a first and second time at the pressure sensor from when the volume of fluid is not in communication with the pressure sensor to when the volume of fluid is in communication with the pressure sensor, determining the volume of fluid within the container or a presence or absence of a fluid connection to the fluid pathway based on the change in pressure values, and executing a response action if the volume of fluid within the container is not within an authorized range of volumes for the time period, or if the presence or absence of a fluid connection is not authorized.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may verify that a solution containing a correct fluid volume is connected to the correct fluid pathway during a fluid processing procedure.

Some embodiments may enable verification of a solution container's correct connection to the intended fluid pathway prior to drawing fluid into the fluid pathway and thereby minimize waste of disposable circuits in biological fluid processing.

Some embodiments may improve monitoring of the timing of solution container installation on a fluid processing hardware to ensure that a solution container is installed at the correct stage of the fluid procedure.

There have been continuing efforts to automate the apparatus and systems used in the collection and/or processing of blood and blood components, and an automated blood component separator for such collection/processing may be employed. One class of such automated separators employs relatively rotating surfaces, at least one of which carries a porous membrane. An example of such a membrane separator is disclosed in PCT Patent Application Publication No. WO 2014/039086 A1, which is incorporated by reference in its entirety, although any suitable membrane separator may be used. Another class employs a centrifuge that utilizes centrifugal separation principles. An exemplary centrifugal separator is disclosed in U.S. Pat. Nos. 5,868,696 and 6,582,349, which are incorporated by reference in their entireties, although any suitable centrifugal separator may be used.

Both membrane separation and centrifugal separation systems may involve a durable processing system or device used in combination with a disposable processing set or circuit. The durable processing system may include a pump assembly that interacts with one or more of the components of the disposable circuit to draw blood or other bodily fluid from a blood source and move the blood or bodily fluid to another location within the disposable circuit by moving fluid through a fluid flow path.

Figure 1:
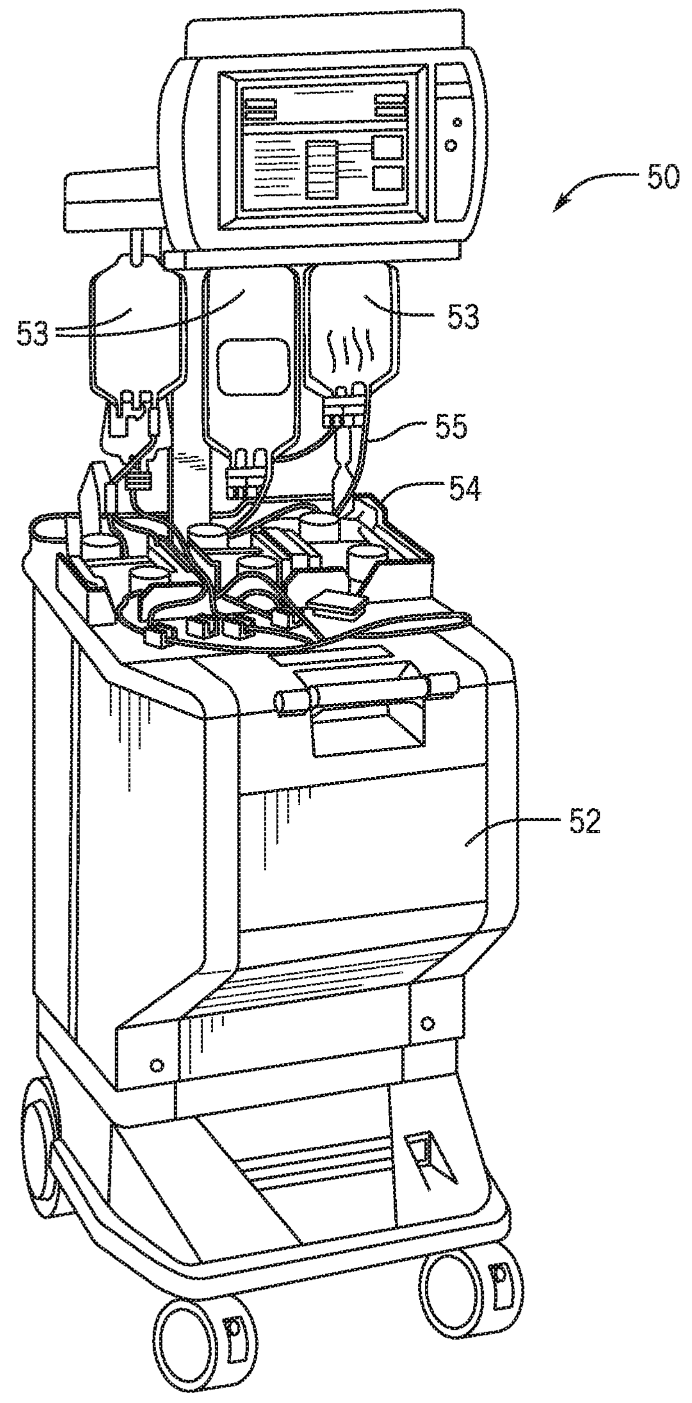
FIG. 1 is a perspective view of an automated medical fluid processing device that may be used in the collection and other processing steps of biological fluids, according to an exemplary embodiment.
Figure 2:
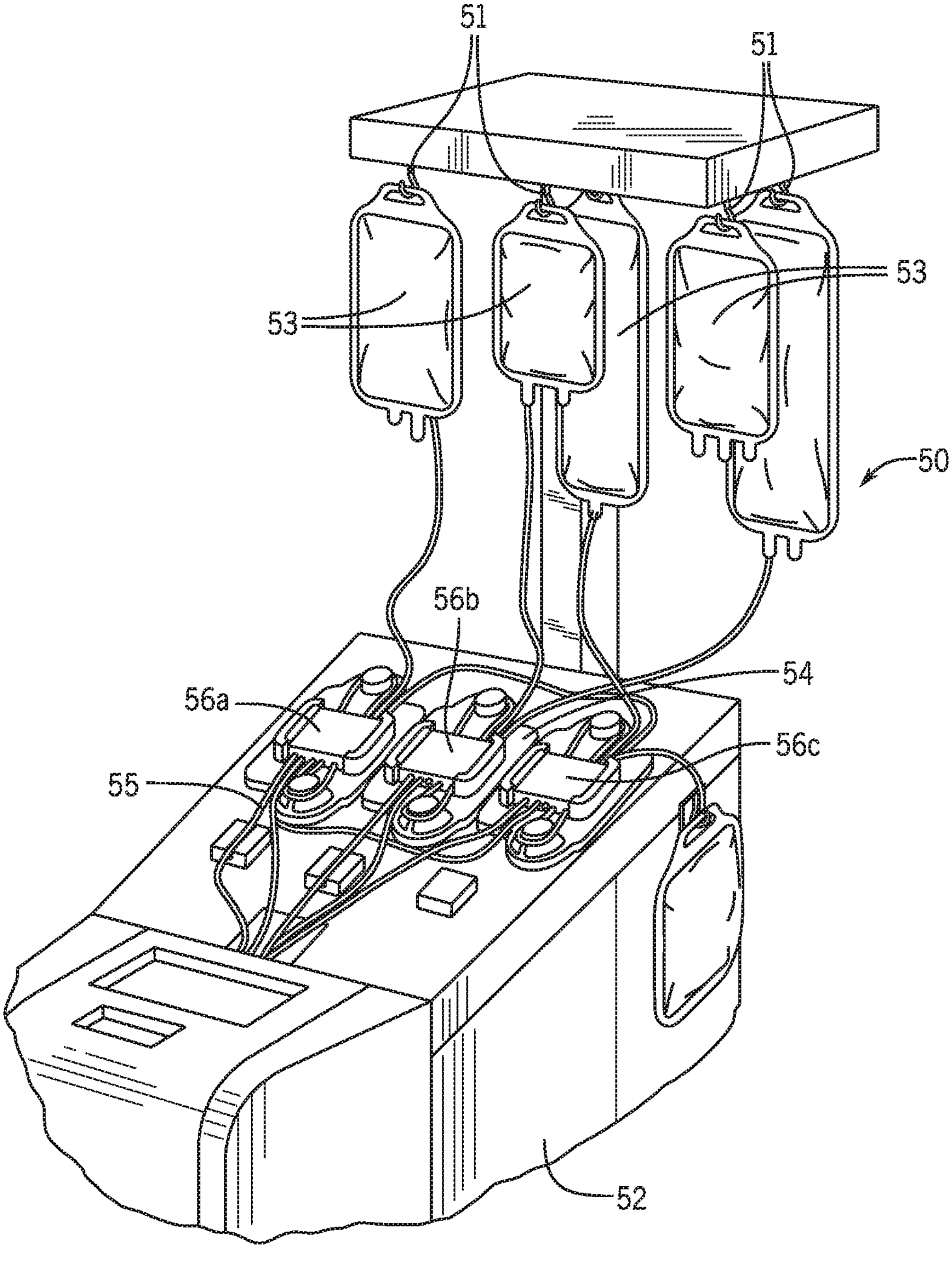
FIG. 2 is an enlarged perspective view of the front panel of the device of FIG. 1 with a disposable processing set mounted on the device, according to an exemplary embodiment.

FIGS. 1 and 2 show an exemplary separation device useful in the separation and processing of blood components, e.g., red blood cells, white blood cells, platelets, plasma, etc. The separator 50 may include a hardware component 52 and a disposable processing kit 54 mounted thereon. In one embodiment, the separation principle used by the separator may be based on centrifugation, but an automated separator based on a different separation principle (e.g., spinning membrane) may also be used.

With respect to the device shown in FIGS. 1 and 2, a rotating centrifuge may be housed within hardware component 52. The hardware component 52 may also comprise a plurality of hangers 51 for hanging fluid containers 53. One or more hangers 51 may also function as a weight scale that is in communication with a pre-programmed controller of the hardware component 52. Disposable kit 54 may include plastic containers 53 for holding fluid, and tubing 55 defining flow paths for movement of the blood, blood components and other medical fluids through the fluid circuit of kit 54. The plastic containers 53 and the tubing 55 may be configured with corresponding access devices (not illustrated), e.g., spike connector, luer connector, cannula, breakaway cannula, etc., to minimize incorrect connections. For example, a saline solution bag may be configured to be accessed by a spike connector, while an anticoagulant bag is configured to be accessed by luer connector.

The disposable processing kit 54 may also include one or more cassettes 56 (i.e., cassettes 56*a*, 56*b* and 56*c* shown in FIG. 2) which may interface with the front panel of hardware component 52. Cassettes 56*a*, 56*b* and 56*c* may include flow paths, pressure sensors, and valve stations. A series of pneumatically or electrically operated valves (numbered 1-10 in FIG. 3, for example) under the control of the pre-programmed controller of hardware component 52 may selectively allow and restrict flow through the flow paths of the cassette and ultimately through the tubing of disposable kit 54. Pressure sensors (numbered PS1-4 in FIG. 3, for example) disposed on the front panel of hardware component 52 may also be in communication with the controller to monitor the fluid procedure. Disposable kit 54 may further include a processing chamber shown generally at 57 of FIG. 3 (which may be mounted on a rotor/spool of the centrifuge). Processing chamber 57 may have a sub-chamber 58 wherein blood or blood components are separated under the influence of centrifugal force (i.e., the "separation chamber') and a sub-chamber 59 where blood components from sub-chamber 58 may be further processed, separated and/or collected (i.e., the "concentration chamber"). In a spinning membrane separation system, the separation chamber and concentration may comprise a spinning membrane separator. Details of an automated separator suitable for use with the systems and methods described herein are set forth in the aforementioned PCT Patent Application Publication No. WO 2014/039086 A1 and U.S. Pat. Nos. 5,868,696 and 6,582,349.

Figure 3:
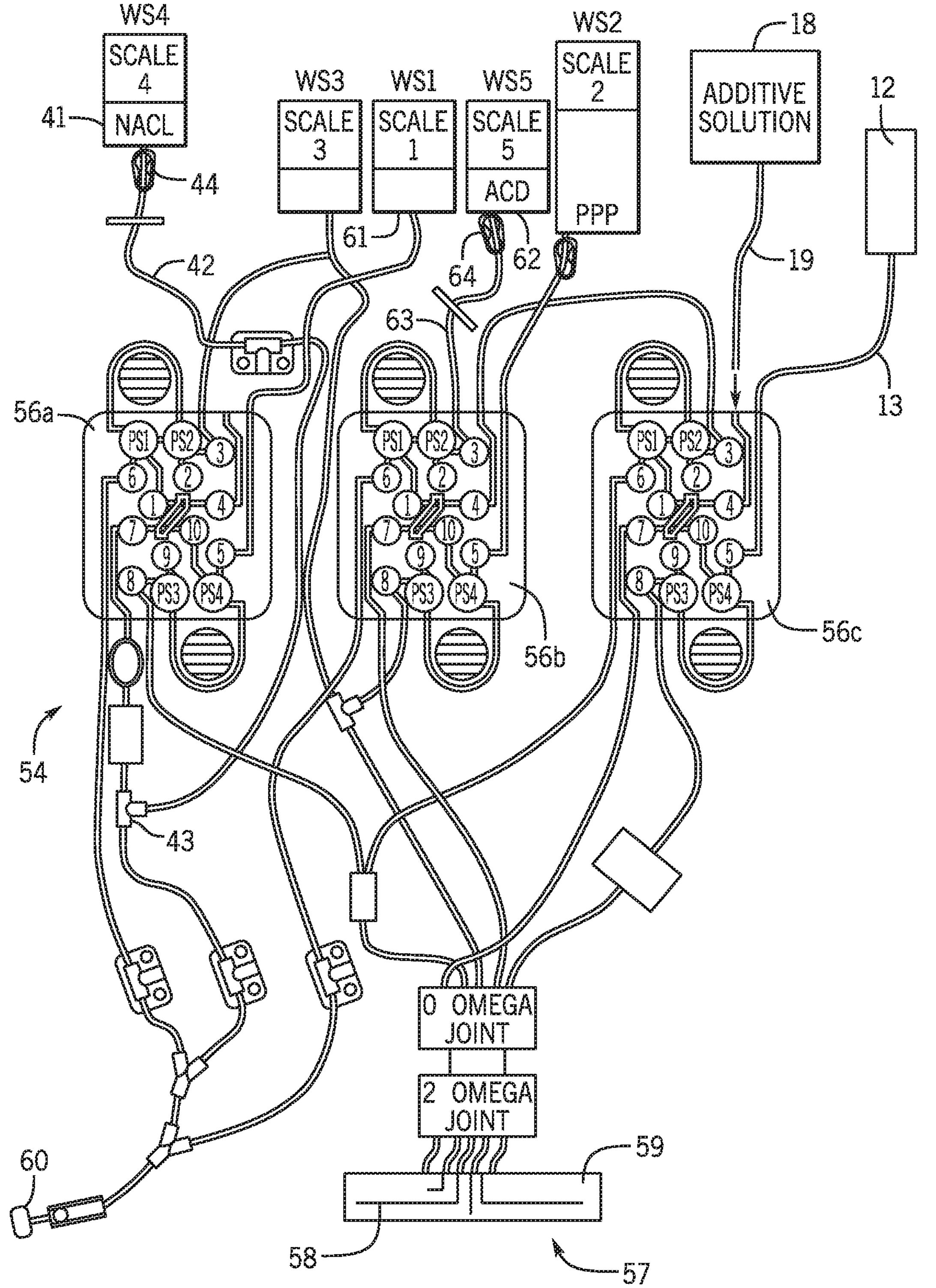
FIG. 3 is a diagram showing a disposable processing set and associated weight scales, according to an exemplary embodiment.

During a particular processing procedure, the pre-programmed controller may operate the separator and processing chamber associated therewith to separate blood into its various components as well as operate one or more pumps and clamps to move blood, blood components, saline, anticoagulant, and/or additive solution through the various openable valves and tubing segments of a processing set 54, such as the one illustrated in FIG. 3. This may include, for example, initiating and causing the separation of red blood cells (RBCs), white blood cells (WBCs), mononuclear cells (MNCs), platelets, and/or plasma from whole blood in a separation chamber and pumping additive solution/saline/anticoagulant from a source through selected valves and tubing segments to prime or purge the tubing segments and/or to displace fluid (such as plasma) that may reside or remain in the tubing. The various processing steps performed by the pre-programmed automated blood processing device may occur separately, in series, simultaneously or any combination of these.

According to an exemplary embodiment, in a first phase of a fluid processing procedure, it may be desirable to prime the disposable kit 54 to purge air from the various fluid pathways of the kit 54. In one embodiment, saline may be used to prime the fluid circuit 54. FIG. 3 depicts a saline container 41 associated with hanger WS4 and connected to cassette 56*a* and pressure sensor PS3 via a fluid path comprising tubing 42, y-connector 43, and valves 7 and 9 of cassette 56*a*. The hanger WS4 may also be a weight scale configured to measure the weight of container 41 and provide input to the controller. The priming phase of one embodiment of a fluid processing procedure may be associated with, e.g., a 1000 mL volume of saline for priming fluid. The controller may be configured to check that the initial weight reading at hanger WS4 at the beginning of the priming phase is within a programmed range, e.g., approximately 900 to 1100 grams for a 1000 mL saline solution. The controller may also be configured to monitor and detect a gradual decrease in weight readings at hanger WS4 and no changes in weight readings at other hangers WS1-3 and WS5 during the priming phase as a confirmation measure that priming fluid is actually exiting the container 41 on hanger WS4 as intended.

Throughout the priming phase, the controller may also be configured to receive input from pressure sensor PS3 to which container 41 may be in fluid communication when the priming phase has initiated. Receiving and checking input from the pressure sensor PS3 may provide a confirmation measure indicating that not only is the saline container 41 hanging on saline hanger WS4, but the saline container 41 is also properly connected to tubing 42 to be in fluid communication with the pressure sensor PS3. A confirmation measure for proper connection to tubing 42 may be advantageous when, for example, the tubing 42 requires manual connection (e.g., via a cannula, luer connection, spike connection, etc.) at any point before or during the fluid procedure or otherwise is not irreversibly connected to the saline container 41 and therefore carries a risk of incorrect connection. Receiving and checking input from the pressure sensor PS3 may also provide earlier feedback when an incorrect connection leads to fluid exiting the wrong container than relying on hanger weight readings alone, which may provide feedback when incorrect fluid has already been substantially drawn into the kit 54, requiring the kit 54 to be discarded.

Figure 4:
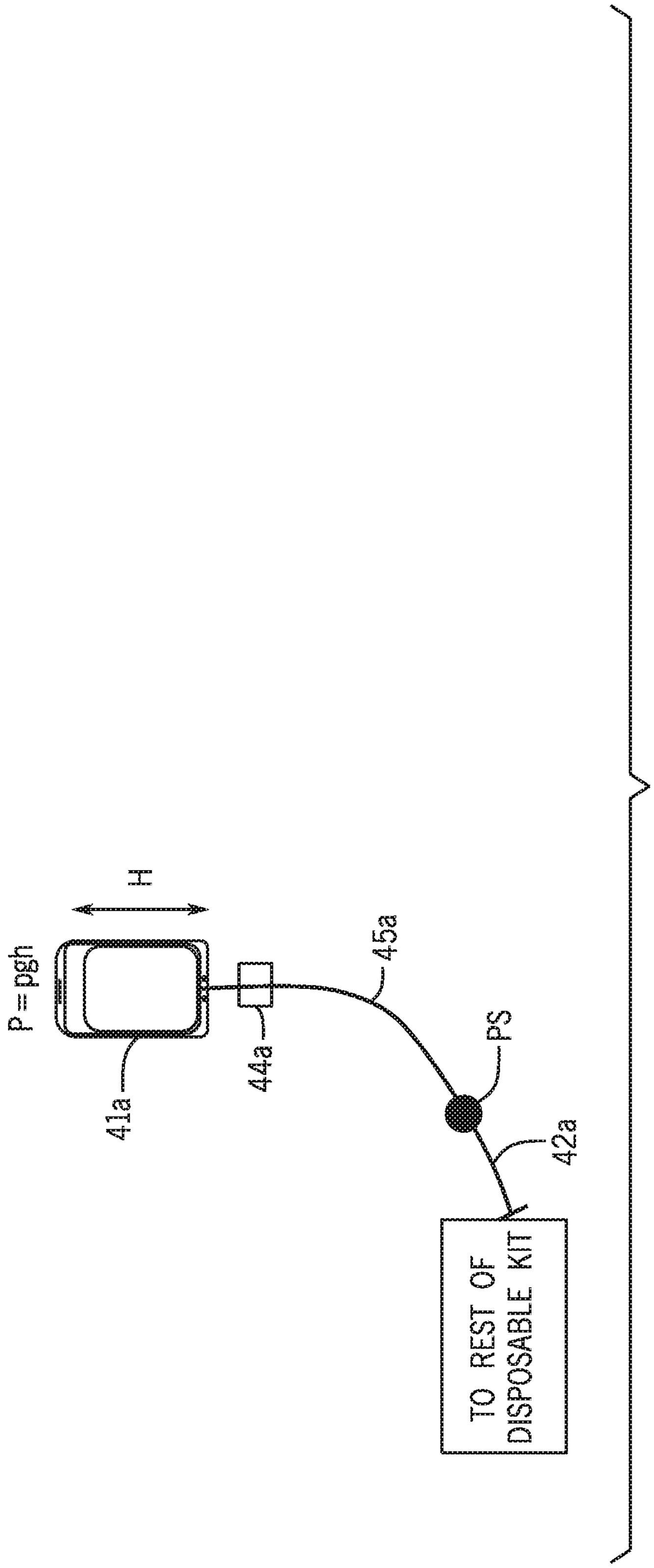
FIG. 4 is a schematic view of a plastic container part of a disposable processing set and its associated fluid pathway in communication with a pressure sensor, according to an exemplary embodiment.
Figure 5:
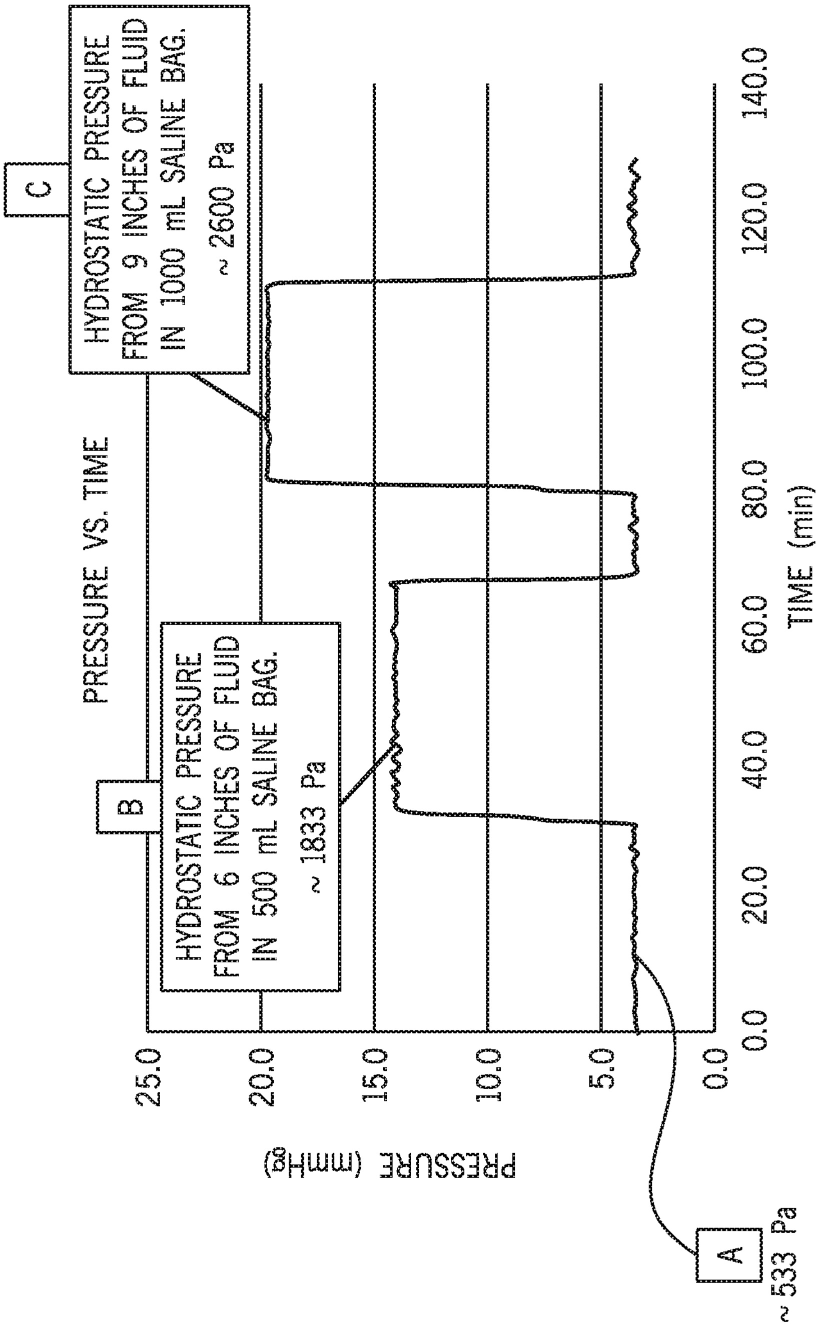
FIG. 5 is a graph of pressure at a pressure sensor plotted over time while connected to multiple volumes of fluid, according to an exemplary embodiment.

Referring to FIGS. 3-5, a process by which the controller may receive hydrostatic pressure input from a pressure sensor, e.g., sensor PS3, and monitor the correct timing and/or identity of fluid flow will be described. Using the fluid path between saline container 41 and pressure sensor PS3 as an example, when the disposable kit 54 is first installed onto the hardware component 52 but prior to initiation of priming, the saline within container 41 may not be in fluid communication with pressure sensor PS3. If container 41 and tubing 42 are initially disconnected, an access device may establish fluid communication at the appropriate time of the procedure. If container 41 and tubing 42 are initially connected, a clamp 44 or similar device may cut off fluid communication until the fluid is required, e.g., at the priming phase. Referring to FIG. 4, during the time when fluid communication is disconnected by clamp 44*a* between container 41*a* and pressure sensor PS, the pressure sensor PS may produce baseline pressure readings, e.g., reflective only of atmospheric pressure or a designated baseline pressure. FIG. 5 is an exemplary pressure versus time graph indicating pressure readings at pressure sensor PS. Point A on the graph in FIG. 5 is representative of the baseline pressure during which fluid communication has been cut off between the container 41*a* and the sensor PS. FIG. 5 shows the baseline pressure being approximately 4 mm Hg, but it should be understood that the baseline pressure may be different for each type of kit and/or may be calibrated independently at the time of each fluid procedure or each phase.

At the start of the priming phase, fluid communication may be established, e.g., by opening clamp 44*a*, and the fluid within container 41*a* may immediately exert pressure against the air column 45*a*, leading to an increased pressure reading at pressure sensor PS. The pressure reading will be largely determined by the hydrostatic pressure of the air column 45*a* and the much larger hydrostatic pressure contributed by the liquid column having height H (FIG. 4) within container 41*a*. The equation for hydrostatic pressure is $P=\rho gh$, where $\rho$ is the density of the fluid, g is the gravitational acceleration, and h is the height of the fluid column exerting the hydrostatic pressure P. Point B on the graph in FIG. 5 is representative of the pressure measured at sensor PS when fluid communication has been initiated between container 41*a* and the sensor PS in an embodiment in which container 41*a* is filled with 500 mL of saline. FIG. 5 shows that the pressure associated with 500 mL of saline at Point B is approximately 14 mm Hg. The pressure associated with 500 mL of saline may further be designated as a range. For example, for Point B of FIG. 5, a pressure reading within 12-17 mm Hg may be associated with 500 mL of saline provided within a particular container. It should be understood that the pressure associated with 500 mL of saline may be different for different container shapes for container 41*a*. For example, in an embodiment in which the shape of container 41*a* comprises a larger x,y-dimension, the same 500 mL volume of saline will possess a smaller height, leading to a smaller hydrostatic pressure exerted by the saline, as determined by the equation $P=\rho gh$. Different container shapes of various fluid manufacturers may therefore be taken into account by programming into the controller, e.g., via a database table comprising different fluid volumes and their associated H and P values, based on, e.g., product codes, serial numbers, product names, and/or manufacturer code for identification. The H and P values for variously shaped containers commonly used for the fluid procedure may be empirically derived and programmed into the controller. When a particular container is to be used for the fluid procedure, the container information may be inputted or scanned into the system at the beginning of the procedure.

Point C on the graph in FIG. 5 is representative of the pressure measured at sensor PS when fluid communication has been initiated between container 41*a* and the sensor PS in an alternate embodiment in which container 41*a* is filled with 1000 mL of saline. FIG. 5 shows that the pressure associated with 1000 mL of saline at Point C is approximately 20 mm Hg, but it should be understood that the pressure associated with 1000 mL of saline may be different for different container shapes for container 41*a*, as explained previously. For both 500 mL and 1000 mL fluid volumes and any other fluid volume, it may be desirable for the controller to verify fluid connection based on pressure readings taken by the pressure sensor PS as soon as fluid communication is established between container 41*a* and the sensor PS prior to substantial fluid being drawn into the tubing 42*a* and the kit 54 from container 41*a*. Utilizing pressure readings as soon as possible may not only allow for minimal contamination of the kit 54 in the event of an incorrect connection or incorrect fluid flow timing and therefore maximize kit salvageability, but the variability in measurement of the pressure readings at points B and C (as determined by the equation $P=\rho gh$) may also be minimized by measuring pressure when the height H of the liquid column is at its lowest, i.e. before any liquid enters a length of tubing 42*a* that would contribute to height h.

The controller may then be configured to compare the measured pressure readings against authorized pressure ranges programmed for the fluid procedure and execute a response action if the measures pressure readings are not within the authorized ranges at specific times. The controller may also be configured to measure pressure at other pressure sensors, e.g., PS1-2 and PS4 of cassette 56*a*, PS1-4 of cassette 56*b*, and/or PS1-4 of cassette 56*c*, to which it is connected to ensure that solutions that should not be connected during a particular phase is not connected at that time. A response action may comprise the controller terminating the procedure, pausing the procedure, alerting the operator of the error, and/or prompting the operator to enter credentials for manual override.

Referring to FIG. 3, in a source fluid drawing phase of the fluid processing procedure subsequent to priming, fluid may be drawn from a fluid source into the disposable kit 54 prior to separation. The fluid source may be a patient connected to access device 60, or the fluid source may be from a source container such as container 61 on hanger WS1. In one embodiment, anticoagulant may be mixed with the source fluid prior to entering processing chamber 57 for separation. FIG. 3 depicts an anticoagulant container 62 associated with hanger WS5 and connected to cassette 56*b* and its pressure sensor PS2 via a fluid path comprising tubing 63 and valve 3 of cassette 56*b*. The hanger WS5 may also be a weight scale configured to measure the weight of container 62 and provide input to the controller. The drawing phase of one embodiment of the fluid processing procedure may be associated with, e.g., a 500 mL volume of anticoagulant for mixing with the source fluid. The controller may be configured to check that the initial weight reading at hanger WS5 at the beginning of the drawing phase is within a programmed range, e.g., approximately 400 to 600 grams for a 500 mL anticoagulant solution. The controller may also be configured to monitor and detect a gradual decrease in weight readings at hanger WS5 and, in the case of source fluid being drawn from a donor/patient, no changes in weight readings at other hangers WS1-4 during the drawing phase as a confirmation measure that anticoagulant is actually exiting the container 62 on hanger WS5 as intended. In an embodiment in which the source fluid is being drawn from a container, e.g., container 61 on hanger WS1, the controller may also be configured to detect a second gradual decrease in weight readings at hanger WS1.

Throughout the drawing phase, the controller may also be configured to receive input from pressure sensor PS2 of cassette 56*b* to which container 62 may be in fluid communication when the drawing phase has initiated. Receiving and checking input from the pressure sensor PS2 may provide a confirmation measure indicating that not only is the anticoagulant container 62 hanging on hanger WS5, but the anticoagulant container 62 is also properly connected to tubing 63 to be in fluid communication with the pressure sensor PS2 of cassette 56*b*. A confirmation measure for proper connection to tubing 63 may be advantageous for reasons described earlier, and the process by which the controller may receive hydrostatic pressure input from the pressure sensor PS2 of cassette 56*b* may likewise be similar to that described for the priming phase.

During the time when fluid communication is not initially established between container 62 and pressure sensor PS2, the pressure sensor PS2 may produce baseline pressure readings, e.g., reflective only of atmospheric pressure or a designated baseline pressure. At the start of the drawing phase, fluid communication may be established, e.g., by opening clamp 64 (FIG. 3), and the pressure sensor PS2 may immediately measure an increased pressure due to the hydrostatic pressure of the anticoagulant solution. The controller may then be configured to compare the increased pressure against authorized pressure ranges programmed for the drawing phase and execute a response action if the increased pressure readings are not within the authorized ranges at specific times. The controller may also be configured to measure pressure at other pressure sensors, e.g., PS1-4 of cassette 56*a*, PS1 and PS3-4 of cassette 56*b*, and/or PS1-4 of cassette 56*c*, to which it is connected to ensure that solutions that should not be connected during a particular phase is not connected at that time. A response action may comprise the controller terminating the procedure, pausing the procedure, alerting the operator of the error, and/or prompting the operator to enter credentials for manual override.

Referring to FIG. 3, after the drawing phase, the source fluid may be separated within the chamber 57 into various components, some of which may be collected and/or returned to the donor. In this return and collection phase of the fluid processing procedure subsequent to separation, collected components may comprise platelets, RBCs, MNCs, plasma, and/or any combination of these. In one illustrative embodiment, platelets may be collected in container 12, and remaining components may be returned to the donor. Additive solution in container 18 may be added to the collected platelets for storage, and as a safety requirement, the donor should be disconnected from the fluid circuit 54 before additive solution is added. FIG. 3 depicts an embodiment in which no weight scales are associated with containers 12 and 18, although weight scales may be present. Containers 12 and 18 may be hung vertically above the cassette 56*c*. The platelet collection container 12 may be connected to pressure sensor PS4 of cassette 56*c* via a fluid path comprising tubing 13 and valve 5 of cassette 56*c*. The additive solution container 18 may be configured for connection to pressure sensor PS2 of cassette 56*c* via a fluid path comprising tubing 19 and valves 4 and 2 of cassette 56*c*. The return and collection phase may be associated with, e.g., simultaneous collection of platelets and remaining blood components to the donor, followed by disconnection of the donor from the kit 54, followed by addition of 500 mL additive solution to the collected platelets. The controller may at the same time detect and confirm that there are no changes in weight readings at other hangers WVS1-5 during the return and collection phase in an embodiment in which, e.g., all other fluid components are being returned to the donor.

During the return and collection phase, the controller may be configured to receive input from pressure sensors PS4 and PS2 of cassette 56*c*. Receiving and checking input from the pressure sensor PS4 may provide a confirmation measure that the platelets are being properly routed into platelet container 12 and also provide an indication of the volume of platelets collected based on expected pressure readings associated with different volumes within container 12 of a known shape. At a time in which return of fluid to the donor is taking place, the controller may also receive input from the pressure sensor PS2 of cassette 56*c* and confirm that the additive solution is not connected to the pressure sensor PS2.

During the time when fluid communication is not initially established between container 18 and pressure sensor PS2 of cassette 56*c*, the pressure sensor PS2 may measure and confirm only baseline pressure readings. Once the donor has disconnected from the kit 54 and transfer of additive solution in container 18 to the platelets in container 12 is initiated, fluid communication may be established and the pressure sensor PS2 may immediately measure an increased pressure due to the hydrostatic pressure of the additive solution. The controller may then be configured to compare the increased pressure against authorized pressure ranges programmed for the 500 mL solution and confirm that the increased pressure reading is within the authorized ranges. The controller may then check that pressure at PS2 continues to increase as additive solution enters tubing 19 and increases the height of the liquid column contributing to $P=\rho gh$. If the initial increased pressure at PS2 is not within authorized ranges and/or pressure at PS2 does not continuously increase according to authorized ranges at specific times, the controller may be configured to execute a response action, which may comprise the controller terminating the procedure, pausing the procedure, alerting the operator of the error, and/or prompting the operator to enter credentials for manual override. The controller may also be configured to measure pressure at other pressure sensors to which it is connected to ensure that solutions that should not be connected during a particular phase is not connected at that time.

Without limiting the foregoing description, in accordance with one aspect of the subject matter herein, there is provided a fluid processing system for monitoring fluid flow in a medical fluid procedure. A fluid circuit comprises a plurality of fluid pathways configured to mount and associate with a durable processing device controlled by a programmable controller. A pressure sensor is in communication with the programmable controller and a fluid pathway. A container part of the fluid circuit is configured for fluid communication with the pressure sensor and receives a volume of fluid. The controller initiates a phase of the medical fluid procedure associated by the controller with a plurality of ranges of pressure values authorized at specific times for the pressure sensor, receives a first pressure value from the pressure sensor measured at a first time during the phase when the volume of fluid is not in fluid communication with the pressure sensor, receives a second pressure value from the pressure sensor measured at a second time during the phase when the volume of fluid is in fluid communication with the pressure sensor, compares a difference between the second pressure value and the first pressure value to an authorized range of pressure values, and executes a response action if the difference is not within the authorized range of pressure values.

In accordance with a second aspect which may be used or combined with the immediately preceding aspect, the controller is configured to associate the authorized range of pressure values with a net change in volume within the container.

In accordance with a third aspect which may be used or combined with any of the preceding aspects, the durable processing device further comprises a second pressure sensor in communication with the controller and a second fluid pathway configured to connect to a second container. The controller is further configured to receive a third pressure value from the second pressure sensor measured at the first time during the phase, receive a fourth pressure value from the second pressure sensor measured at the second time during the phase, compare a difference between the fourth pressure value and the third pressure value to a second authorized range of pressure values for the second pressure sensor, and execute a response action if the difference between the fourth pressure value and the third pressure value is not within the second authorized range of pressure values.

In accordance with a fourth aspect which may be used or combined with any of the preceding aspects, the durable processing device further comprises a second pressure sensor in communication with the controller and a second fluid pathway configured to connect to a second container. The controller is further configured to receive a third pressure value from the second pressure sensor measured at a third time during the phase, receive a fourth pressure value from the second pressure sensor measured at a fourth time during the phase, and compare a difference between the fourth pressure value and the third pressure value to a second authorized range of pressure values for the second pressure sensor. The authorized range of pressure values between the first and second times is associated by the controller with a first net change in volume within the container, and the second authorized range of pressure values between the third and fourth times is associated by the controller with a second net change in volume within the second container. The controller is further configured to execute a response action if the difference between the fourth pressure value and the third pressure value is not within the second authorized range of pressure values.

In accordance with a fifth aspect which may be used or combined with any of the preceding aspects, the durable processing device further comprises a weight scale configured to weigh the container and the volume of fluid. The controller is further configured to receive a weight value from the weight scale measured at the first time during the phase, compare the weight value to an authorized range of weight values for the weight scale, and execute a response action if the weight value is not within the authorized range of weight values.

In accordance with a sixth aspect which may be used or combined with the immediately preceding aspect, the durable processing device further comprises a second weight scale configured to weigh a second container and a second volume of fluid configured for fluid communication with a second fluid pathway of the fluid circuit. The controller is further configured to receive a second weight value from the second weight scale measured at the first time during the phase, compare the second weight value to a second authorized range of weight values for the second weight scale, and execute a response action if the second weight value is not within the second authorized range of weight values.

In accordance with a seventh aspect which may be used or combined with any of the preceding aspects, the volume of fluid comprises at least one of blood, blood components, saline, anticoagulant, and additive solution.

In accordance with an eighth aspect which may be used or combined with any of the preceding aspects, the second time during the phase is when fluid communication between the volume of fluid and the pressure sensor is first established, In accordance with a ninth aspect which may be used or combined with any of the preceding aspects, the controller is further configured to select the authorized range of pressure values based on inputted information of at least one of the container's product code, serial number, product name, manufacturer name, and manufacturer code.

In accordance with a tenth aspect which may be used or combined with any of the preceding aspects, the response action comprises at least one of terminating the fluid procedure, pausing the fluid procedure, alerting an operator of an error, and prompting the operator to enter credentials for manual override.

In accordance with an eleventh aspect, there is provided a computer-implemented method for operating and monitoring a medical device and its disposable component used in a fluid procedure. The method comprises providing a fluid circuit comprising a plurality of fluid pathways configured to mount and associate with a durable processing device controlled by a programmable controller. The durable processing device comprises a pressure sensor in communication with the programmable controller and a fluid pathway. A container part of the fluid circuit is configured for fluid communication with the pressure sensor and configured to receive a volume of fluid. The method also comprises measuring a change in pressure values between a first and second time at the pressure sensor from when the volume of fluid is not in communication with the pressure sensor to when the volume of fluid is in communication with the pressure sensor, determining the volume of fluid within the container or a presence or absence of a fluid connection to the fluid pathway based on the change in pressure values, and executing a response action if the volume of fluid within the container is not within an authorized range of volumes for the time period, or if the presence or absence of a fluid connection is not authorized.

In accordance with a twelfth aspect which may be used or combined with the immediately preceding aspect, the volume of fluid comprises a height at the first time and comprises the same height at the second time.

In accordance with a thirteenth aspect which may be used or combined with any of the eleventh through twelfth aspects, the method further comprises providing as part of the durable processing device a second pressure sensor in communication with the programmable controller and a second fluid pathway of the fluid circuit configured to connect to a second container configured to receive a second volume of fluid. The method also comprises measuring a second change in pressure values between the first and second times at the second pressure sensor, determining the second volume of fluid connected to the second fluid pathway based on the second change in pressure values, and executing a response action if the second volume of fluid is not within a second authorized range of volumes at the second pressure sensor.

In accordance with a fourteenth aspect which may be used or combined with the eleventh through thirteenth aspects, the method further comprises providing as part of the durable processing device a second pressure sensor in communication with the programmable controller and a second fluid pathway of the fluid circuit configured to connect to a second container. The method also comprises measuring a second change in pressure values between a third and fourth time at the second pressure sensor, and determining a change in volume of fluid within the second container based on the second change in pressure values.

In accordance with a fifteenth aspect which may be used or combined with the immediately preceding aspect, the method also comprises executing a response action if the change in volume of fluid within the second container is not an authorized change in volume between the third and fourth times at the second pressure sensor.

In accordance with a sixteenth aspect which may be used or combined with the eleventh through fifteenth aspects, the method further comprises providing as part of the durable processing device a weight scale configured to weigh the container and the volume of fluid. The method comprises measuring a weight value from the weight scale at the first time, determining the volume of fluid within the container based on the weight value, and executing a response action if the volume of fluid is not within an authorized range of volumes.

In accordance with a seventeenth aspect which may be used or combined with any of the eleventh through sixteenth aspects, the volume of fluid comprises at least one of blood, blood components, saline, anticoagulant, and additive solution.

In accordance with an eighteenth aspect which may be used or combined with any of the eleventh through seventeenth aspects, the second time is when fluid communication between the volume of fluid and the pressure sensor is first established.

In accordance with a nineteenth aspect which may be used or combined with any of the eleventh through eighteenth aspects, determining the volume of fluid within the container from the change in pressure values is based on inputted information of at least one of the container's product code, serial number, product name, manufacturer name, and manufacturer code.

In accordance with a twentieth aspect which may be used or combined with any of the eleventh through nineteenth aspects, the response action comprises at least one of terminating the fluid procedure, pausing the fluid procedure, alerting an operator of an error, and prompting the operator to enter credentials for manual override.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A bodily fluid separation device for use in combination with a fluid circuit comprising a plurality of containers including a fluid container and a fluid conduit connected to the fluid container, the bodily fluid separation device comprising:

a pump configured to be actuated to draw a fluid from the fluid container via the fluid conduit;

a sensor configured to monitor a portion of the fluid conduit positioned between the fluid container and the pump; and a controller configured to initiate a priming phase of a bodily fluid separation procedure in which the pump is actuated to draw the fluid from the fluid container via the fluid conduit, and receive at least one measurement from the sensor during the priming phase to determine whether the fluid container is properly connected to the fluid conduit to be in fluid communication with the sensor.

2. The bodily fluid separation device of claim 1, wherein the controller is further configured to determine whether the fluid container is a priming fluid container and the fluid is a priming fluid based at least in part on said at least one measurement.

3. The bodily fluid separation device of claim 2, wherein the controller is configured to determine whether the fluid container is a saline container based at least in part on said at least one measurement.

4. The bodily fluid separation device of claim 1, further comprising a hanger configured to support the fluid container.

5. The bodily fluid separation device of claim 4, further comprising a weight scale associated with the hanger.

6. The bodily fluid separation device of claim 5, wherein the controller is configured to receive measurements from the weight scale during the priming phase to determine whether the fluid is exiting the fluid container via the fluid conduit.

7. The bodily fluid separation device of claim 5, wherein the controller is configured to receive a measurement from the weight scale to determine whether the fluid container is a priming fluid container.

8. The bodily fluid separation device of claim 7, wherein the controller is configured to compare the measurement from the weight scale to an authorized range of weight values to determine whether the fluid container is a priming fluid container.

9. The bodily fluid separation device of claim 8, wherein the controller is configured to execute a response action when the measurement from the weight scale is not within the authorized range of weight values.

10. The bodily fluid separation device of claim 1, further comprising a clamp or valve configured to engage the fluid conduit at a position between the fluid container and the sensor.

11. The bodily fluid separation device of claim 1, wherein the controller is configured to execute a response action upon determining that the fluid container is not properly connected to the fluid conduit to be in fluid communication with the sensor.

12. The bodily fluid separation device of claim 11, wherein the response action comprises at least one of terminating the bodily fluid separation procedure, pausing the bodily fluid separation procedure, alerting an operator of an error, and prompting the operator to enter credentials for manual override.

13. The bodily fluid separation device of claim 1, further comprising a centrifuge configured to separate a bodily fluid into two or more components during said bodily fluid separation procedure.

14. The bodily fluid separation device of claim 1, wherein said at least one measurement comprises a first measurement from the sensor measured at a first time when the fluid container is not in fluid communication with the portion of the fluid conduit monitored by the sensor, and a second measurement from the sensor measured at a second time when the fluid container is in fluid communication with the portion of the fluid conduit monitored by the sensor.

15. The bodily fluid separation device of claim 14, wherein the second time is when fluid communication between the fluid container and said portion of the fluid conduit is first established.

16. The bodily fluid separation device of claim 14, wherein the controller is configured to compare a difference between the second measurement and the first measurement to determine whether the fluid container is properly connected to the fluid conduit to be in fluid communication with the sensor.

17. The bodily fluid separation device of claim 16, wherein the controller is configured to compare the difference to an authorized range of values to determine whether the fluid container is properly connected to the fluid conduit to be in fluid communication with the sensor.

18. The bodily fluid separation device of claim 17, wherein the controller is configured to execute a response action when the difference is not within the authorized range of values.

19. The bodily fluid separation device of claim 17, wherein the controller is configured to select the authorized range of values based on inputted information of at least one of the fluid container's product code, serial number, product name, manufacturer name, and manufacturer code.

20. The bodily fluid separation device of claim 1, wherein the sensor comprises a pressure sensor.

* * * * *